United States Patent
London et al.

(10) Patent No.: US 9,891,301 B2
(45) Date of Patent: Feb. 13, 2018

(54) APPARATUS AND METHODS FOR DYNAMICAL TRACKING OF MECHANICAL ACTIVITY WITHIN CELL POPULATIONS

(71) Applicant: University of Iowa Research Foundation, Iowa City, IA (US)

(72) Inventors: Barry London, Iowa City, IA (US); Vladimir Shusterman, Pittsburgh, PA (US); Xiaodong Zhu, Pittsburgh, PA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 15/267,868

(22) Filed: Sep. 16, 2016

(65) Prior Publication Data

US 2017/0082717 A1    Mar. 23, 2017

Related U.S. Application Data

(60) Provisional application No. 62/220,753, filed on Sep. 18, 2015.

(51) Int. Cl.

| | |
|---|---|
| *G06K 9/00* | (2006.01) |
| *G01R 33/563* | (2006.01) |
| *G01N 33/483* | (2006.01) |
| *G01N 24/08* | (2006.01) |
| *G01R 33/465* | (2006.01) |
| *G01R 33/54* | (2006.01) |
| *G01R 33/30* | (2006.01) |
| *G01R 33/31* | (2006.01) |

(52) U.S. Cl.
CPC ....... *G01R 33/56308* (2013.01); *G01N 24/08* (2013.01); *G01N 33/4833* (2013.01); *G01R 33/30* (2013.01); *G01R 33/31* (2013.01); *G01R 33/465* (2013.01); *G01R 33/543* (2013.01)

(58) Field of Classification Search
CPC .. G01R 33/56308; G01R 33/31; G01R 33/30; G01R 33/543; G01R 33/465; G01N 33/4833; G01N 24/08
See application file for complete search history.

(56) References Cited

U.S. PATENT DOCUMENTS

| | | | | |
|---|---|---|---|---|
| 4,712,560 A | * | 12/1987 | Schaefer ............ | G01R 33/5676 324/309 |
| 2010/0191099 A1 | * | 7/2010 | Salerno ................. | A61B 5/055 600/420 |
| 2014/0030753 A1 | * | 1/2014 | Othman ................ | C12M 41/46 435/29 |
| 2014/0210465 A1 | * | 7/2014 | Kim .................... | G01R 33/3635 324/309 |

(Continued)

OTHER PUBLICATIONS

Chen et al. Measuring collective cell movement and extracellular matix interactions using magnetic resonance imaging, Scientific Reports, May 23, 2013, pp. 1-9.*

(Continued)

*Primary Examiner* — John Strege
(74) *Attorney, Agent, or Firm* — Schwegman Lundberg & Woessner, P.A.

(57) ABSTRACT

Apparatus and methods for dynamical tracking of movement of cells and cell groups within cell populations using magnetic resonance imaging are provided.

19 Claims, 5 Drawing Sheets

(56) References Cited

U.S. PATENT DOCUMENTS

2014/0371574 A1    12/2014   Shusterman et al.
2015/0141791 A1*    5/2015   O'Neill .............. A61B 5/04085
                                                        600/391

OTHER PUBLICATIONS

Costet, Alexandre, et al., "Electromechanicalwave Imaging of Biologicallyand Electrically Paced Canine Hearts in Vivo", Ultrasound in Med. & Biol., vol. 40, No. 1, (2014), 177-187.
Mizutani, Ryuta, et al., "X-ray microtomography in biology", Micron 43, (2012), 104-115.
Perkel, Jeffrey M., "Small animal imaging: Data that's more than skin deep", American Association for the Advancement of Science., (Jun. 12, 2015), 16 pgs.
Zlochiver, Sharon, et al., "Electrotonic Myofibroblast-to-Myocyte Coupling Increases Propensity to Reentrant Arrhythmias in Two-Dimensional Cardiac Monolayers", Biophysical Journal vol. 95, (Nov. 2008), 4469-4480.

* cited by examiner

APPARATUS AND METHODS FOR DYNAMICAL TRACKING OF MECHANICAL ACTIVITY WITHIN CELL POPULATIONS

CROSS-REFERENCE TO RELATED APPLICATIONS

This application claims the benefit of the filing date of U.S. application Ser. No. 62/220,753, filed on Sep. 18, 2015, the disclosure of which is incorporated by reference herein.

STATEMENT OF GOVERNMENT RIGHTS

This invention was made with government support under grant DP1OD003819 awarded by the National Institutes of Health. The government has certain rights in the invention.

BACKGROUND

Two/three-dimensional (2/3D) multicellular constructs (MTCs), which consist of inter-connected and structurally organized cell populations, are widely used in various fields of regenerative medicine, biotechnology, and drug testing or development. For example, the patterns of electrical and mechanical activity in cardiomyocytes, and the coupling between them, are essential for normal functioning of the heart; their disruption usually signifies a diseased state. Cultured MTCs serve as models for studying electrical and mechanical properties of cardiac tissues in controlled conditions that replicate salient features of their natural environment, providing insight into the normal physiology and pathogenesis of heart diseases. In particular, they provide models for studying the mechanisms of cardiac arrhythmias and heart failure and serve as a tool for investigating the effects of molecular, genetic, pharmacological, and nonpharmacological interventions. However, technologies for noninvasive (nondestructive) functional evaluation of internal cell structures within such 2D and 3D MTCs are limited to X-ray microtomography (micro-CT) and a few other X-ray and ultrasound-based imaging modalities. Most of these methods do not provide high-quality soft-tissue characterization and often require injection of toxic substances for improved tissue contrast ("tagging") (Perkel et al., 2012; Mizutani et al., 1993). In addition, the use of ionizing radiation in micro-CT and other X-ray based imaging is not appropriate for longer-duration, real-time functional imaging studies.

SUMMARY

This disclosure provides an apparatus and methods for dynamical tracking of mechanical activity (movement) of cells, cell groups or subpopulations within cell populations using magnetic resonance imaging (MRI). The apparatus and method overcome several technological challenges. MRI scanners are typically used for the imaging of static objects, because MRI has a limited temporal resolution (due to the need to collect and analyze the frequency content of the received signals in order to generate an image). Applications of dynamical MRI are currently limited to movement of relatively large objects, such as heart movements. Due to relatively low signal-to-noise ratio, spatial resolution of the dynamical MRI is limited to an approximately millimeter-to-centimeter scale. Since the MRI of mechanical activity of cells, cell groups or subpopulations within cell populations requires a higher (submillimeter) resolution, the dynamic MRI of such movement has not been described.

Figure 1:
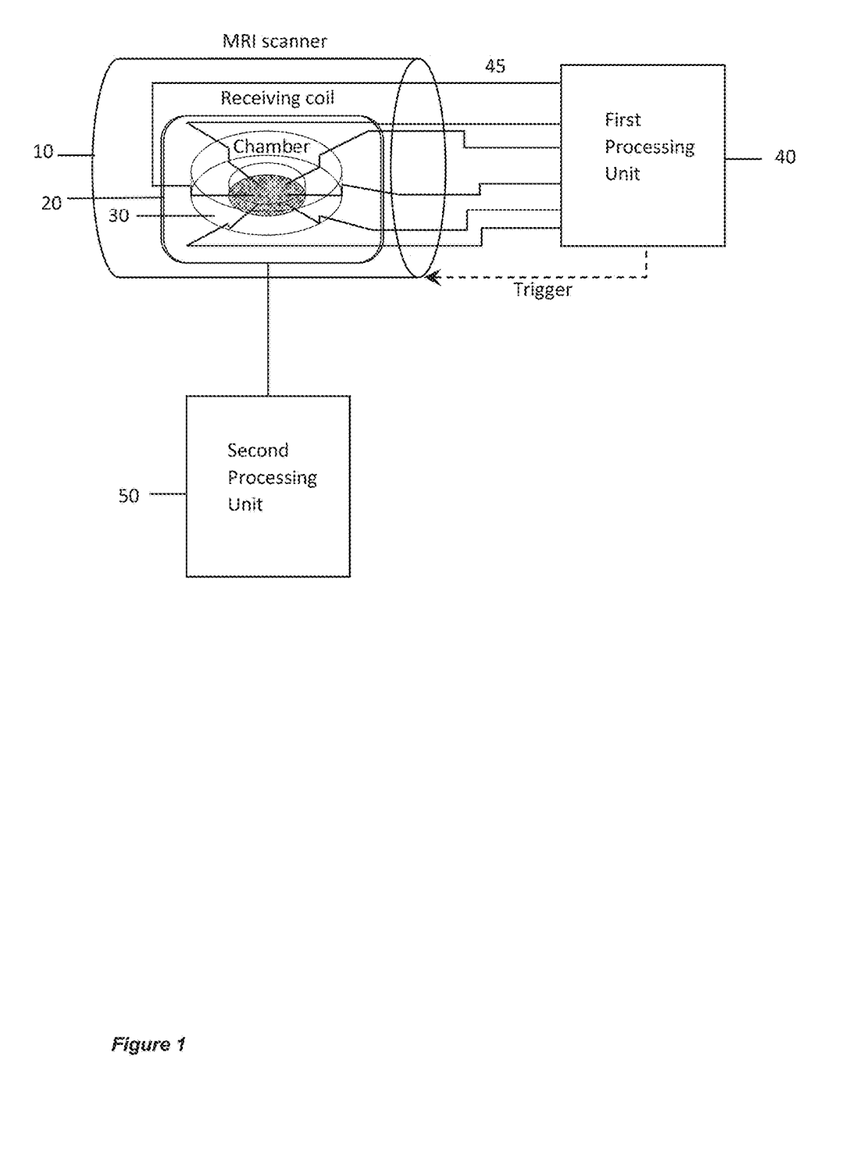
FIG. 1. A block-diagram of one embodiment, comprising an MRI receiving coil (20) located inside an MRI scanner (10), cell chamber (30) with a population of cardiac cells, first processing unit (40) with MRI compatible electrodes (45), and second processing unit (50).

In one embodiment, the disclosure provides an apparatus. A block diagram of an exemplary apparatus is shown in FIG. 1. The apparatus includes a MRI receiving coil (20) located at the isocenter of MRI scanner (10), a cell chamber (30) with a population of cells, e.g., cardiac cells, located inside the receiving coil (20), and a first processing unit (40) connected to MRI-compatible electrodes (45), which extend inside the cell chamber (30) to make electrical contact with the cell population, register cells' electrophysiological activity, and perform electrical pacing. The first processing unit receives and analyzes cell electrophysiological activity in real time to determine phases of cell electrophysiological activity cycle and to synchronize (trigger) the MRI scanner's (10) operation (imaging) with specific phases of that activity cycle. A second processing unit (50) receives MRI data from the receiving coil (20), processes MR images acquired during different phases of the cell activity cycle, and displays a sequence of the MR images to reproduce the speed and pattern of movement of cells, cell groups or subpopulations within cell populations.

Figure 2A:
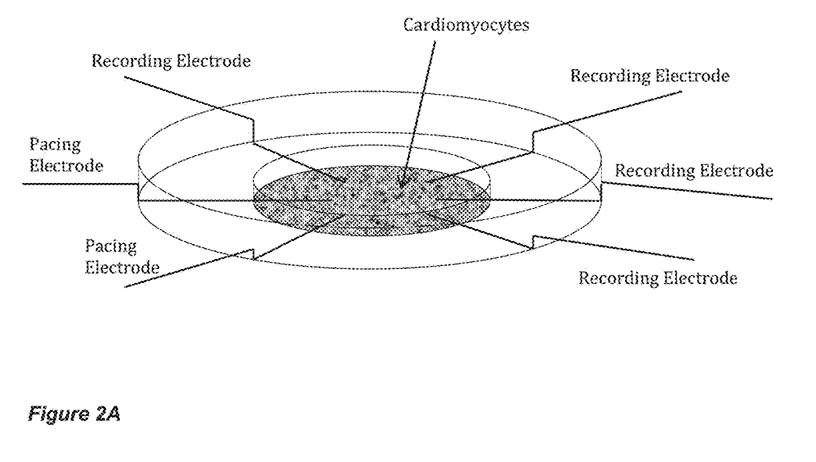
FIGS. 2A-B. A) Cell chamber with MRI-compatible recording and pacing electrodes. B) Cell chamber with MRI-compatible recording and pacing electrodes and a heating pad.
Figure 2B:
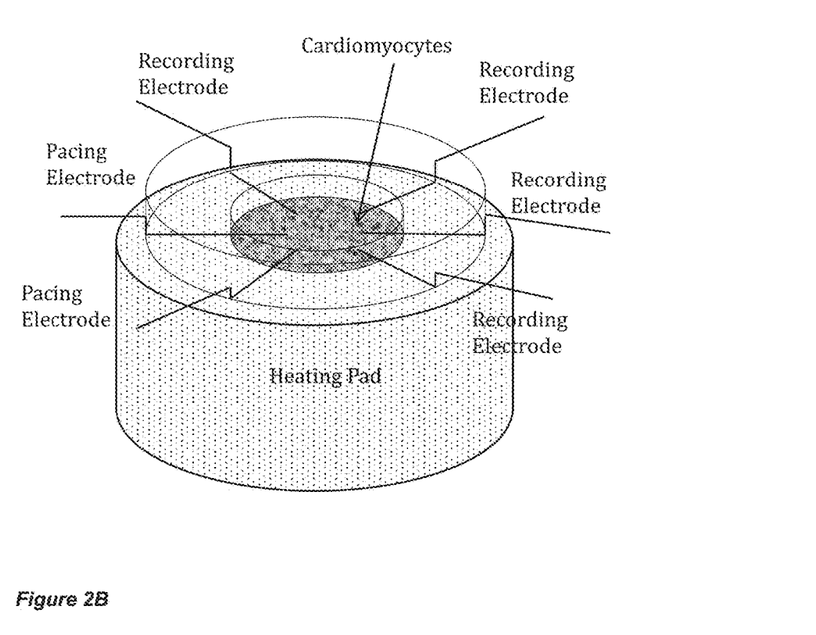

In one embodiment, the synchronization of scanning with the phases of cell activity level applies to the initiation of MRI pulse sequences, specifically the initiation of radiofrequency pulses. In another embodiment, the synchronization applies to the activation of MRI gradient magnetic fields. In some embodiments, synchronization applies to the timing of MRI signal acquisition. In one embodiment, synchronization applies to the timing of passive MRI signal acquisition, which is performed without radiofrequency pulses. During MRI, the cell chamber may be placed on an MRI-compatible heating pad, such as one shown in FIG. 2.

This disclosure provides for an increase in imaging resolution and signal-to-noise ratio. In one embodiment, the apparatus minimizes the distance between the imaged cells and the receiving coil by fitting the cell chamber inside the coil and/or adapting the receiving coil to the geometry of the cells and cell chamber. The electrical activity of cells may be used for synchronizing the MRI to the specific phases of a cycle, e.g., a cardiac cycle. In one embodiment, cell electrophysiological activity may be recorded using MRI-compatible electrodes, and processed (in the first processing unit) to analyze waveforms and detect main peaks, such as the main excitation peak (which is similar to the electrocardiographic R-peak on the surface electrocardiogram). The time of these main peaks of electrical excitation may then be used to synchronize (trigger) the MRI scanner's operation and image acquisition with the specific phases of the cycles, e.g., cardiac cycles. To increase the signal-to-noise ratio, the images may be obtained repeatedly during the same phase of the cycles and averaged. A sequence of thus obtained and processed MR images that correspond to various phases of cells' activity cycles is displayed on a computer screen to reproduce the speed and pattern of movement of cells, cell groups or subpopulations within cell populations (e.g., contractions).

Thus, magnetic resonance imaging (MRI) provides a viable, noninvasive, non-toxic method with soft-tissue contrast to analyze MTCs in vitro, e.g., using a MRI-compatible cell chamber and a MRI coil (referred to as a MRI-CCC), as well as cell-imaging software.

For example, rat (Sprague-Dawley) neonatal cardiomyocytes were isolated by collecting hearts from one-day-old pups, mincing, and digesting the hearts with trypsin and collagenase sequentially. Cells were preplated to remove fibroblasts. The cardiomyocyte-enriched cells were placed on a testing plate embedded with MRI-compatible electrodes in culture medium (DMEM/F-12 with L-glutamine and HEPES containing 5% horse serum, 1×Gibco® Insulin-Transferrin-Selenium (ITS-G), and 1×penicillin-streptomycin). The cardiomyocytes were cultured for 3-5 days in the same medium and used for imaging. For the electromechanical imaging experiments, the testing plate was placed inside an MRI receiving coil and moved into the scanner isocenter, and a high-fidelity, MR-compatible, wireless, 12-lead electrophysiological recording system with MRI-compatible electrodes was used for continuous data recording during electromechanical imaging experiments.

The present invention thus enables functional characterization and monitoring of cell constructs such as MTCs in the MRI environment. In one embodiment, the invention provides a system having a cell chamber with an external compartment (which interacts with non-sterile, external environment) and an internal compartment (which contains the cells), in communication with electrodes, e.g., ones that can withstand autoclaving. In one embodiment, the system is employed to track mechanical activity and/or electrical activity in cardiac MTCs, which serve as models for studying properties of cardiac tissues in controlled conditions and for testing cardioactive drugs.

Methods, systems and apparatus for imaging, and measuring and/or recording, activities of multicellular constructs in culture are provided. The methods may employ magnetization and its relaxation-based measurements, sensitive or specifically sensitized to the properties of electrical activity, to determine the spatio-temporal distribution of electromagnetic field and electrical potentials in multicellular constructs in culture, and to display such spatio-temporal distribution (image). In one embodiment, the system uses external (to the multicellular constructs) magnets, gradient magnetic fields or radio-frequency waves, such as those commonly used for MRI, to generate the magnetic resonance. The methods and systems may employ the magnetization and its relaxation-based measurements to detect mechanical activity in multicellular constructs in culture, and to display that activity (image).

In one embodiment, the system includes (i) cell-feeding tubes/tube openings, in communication with a MTC holding chamber, e.g., a culture dish, (ii) an MRI-compatible heating unit, e.g., heating pad, (iii) an MRI-compatible recording device, e.g., video camera, and/or (iv) MRI-compatible electrodes for electrophysiological monitoring including recording and pacing electrodes.

In one embodiment, the invention provides a method to non-invasively, simultaneously detect mechanical activity and electrical activity in cells in vitro. The method includes providing a population of cells in a substrate (a receptacle such as a culture dish) in communication with one or more magnetic resonance imaging (MRI)-compatible electrodes; applying a magnetic resonance (MR) pulse sequence to the cells; and simultaneously recording electrical activity using the one or more electrodes and imaging mechanical activity using MRI. In one embodiment, the population of cells is in a monolayer. In one embodiment, the population of cells forms structure having dimensions (height, length, width) independently from about 1 mm to 100 mm, or from about 1 cm to about 10 cm. In one embodiment, the cells are cardiomyocytes, smooth muscle cells or skeletal muscle cells, or stem cells. In one embodiment, the cells are induced pluripotent stem cells (iPSCs). In one embodiment, the cells are cells from a patient with a disorder, e.g., a cardiac disorder, or an animal model of a human disorder. In one embodiment, the cells are genetically modified, e.g., augmented with a recombinant DNA construct or having a deletion, e.g., one that knocks out function of a gene product, such as cells from a transgenic or knock out animal, such as a mouse, rat, rabbit or pig, model of human disease, e.g., a model of high blood pressure or valve dysfunction. In one embodiment, the cells are exposed to one or more compounds prior to simultaneous imaging and recording. In one embodiment, electrical excitation and recovery, local conduction block, and/or reentry, which can be produced by the application of calcium blockers and other pharmacological agents to cardiomyoctes, are measured or recorded. In one embodiment, the patterns of electrical excitation are recorded and the patterns of mechanical activities, e.g., contractions, are imaged. Furthermore, MR-based contraction tracking can be extended to MR-based sodium, potassium, and phosphorous imaging, to examine the effects of biologically important ions on electromechanical properties of cardiac tissues. In one embodiment, the one or more electrodes are disposed on a substrate, e.g., a culture dish, having the cells. In one embodiment, the one or more electrodes are in contact with media or with the cells. In one embodiment, the substrate, media or cells are in communication with one or more pacing electrodes. Thus, the method provides for simultaneous tracking of both electrical excitation and mechanical contraction in MTCs on a cell-cluster scale using magnetic resonance imaging (MRI) combined with MR-compatible electrophysiological imaging to evaluate the coupling between electrical excitation and mechanical contraction properties in cells.

This disclosure also provides a method to non-invasively detect structural activity in cells in vitro by applying a magnetic resonance pulse sequence to a population of cells in a substrate and recording the activity of the cells using MR.

Further provided is a method to detect electrical activity in cells in vitro. The method providing a population of cells in a substrate in communication with one or more MRI-compatible electrodes; applying a magnetic resonance pulse sequence to the cells; and recording electrical activity using the one or more electrodes.

The invention also provides a system for non-invasively, simultaneously detecting mechanical activity and electrical activity in cells in vitro comprising: a) a cell culture device comprising a substrate for cells and media, and conduits for introducing and removing the media; b) one or more MRI compatible electrodes in contact with the substrate, cells or media; and c) MRI compatible recording device.

Also provided is an apparatus for simultaneously detecting mechanical activity and electrical activity in cell populations. The apparatus includes a cell chamber (device) configured to contain the cell populations; a plurality of electrodes configured to be coupled to the cell chamber to record the electrical activity; and a recording system including a magnetic resonance imaging (MRI) scanner configured to record the mechanical activity and an electrophysiological recording device configured to be coupled to recording electrodes of the plurality of electrodes to record the electrical activity. The cell chamber, the plurality of electrodes, and the electrophysiological recording device are MRI compatible. In one embodiment, the recording system is configured to conduct electromechanical mapping allowing for evaluation of coupling between electrical excitation and mechanical contraction properties of the cells. In one embodiment, the cell culture device comprises a substrate configured to contain the cells and a medium. In one embodiment, the plurality of electrodes comprises electrodes placed in the media. In one embodiment, the plurality of electrodes are each embedded in the substrate or are each attached to the substrate. In one embodiment, the plurality of electrodes comprises at least two pacing electrodes suitable for delivering cardiac pacing pulses to the cells, and further comprising a pacemaker configured to deliver the cardiac pacing pulses to the cells through the at least two pacing electrodes. In one embodiment, the apparatus further includes an MRI-compatible heater (e.g., heating pad) configured to be coupled to, e.g., by being placed underneath, the cell chamber. In one embodiment, the MRI scanner comprises an isocenter and an MRI receiving coil, and wherein the cell chamber is placed inside the MRI receiving coil and the MRI receiving coil is placed in the isocenter.

DETAILED DESCRIPTION

In one embodiment, an apparatus for dynamical imaging of mechanical activity (movement) of cells, cell groups or subpopulations within cell populations in vitro is provided. The apparatus includes a cell chamber configured to contain cells; a plurality of electrodes (for electrophysiological recording and pacing) configured to be coupled to the cell chamber and extended underneath the cell population to provide electrical contact with the cell population; an electrophysiological recording and processing system (first processing unit) connected to the electrophysiological recording and pacing electrodes; a second processing unit; and an MRI scanner, wherein the cell chamber, the plurality of electrodes, and the first and second processing units are MRI compatible. In one embodiment, the cell chamber is placed inside an MRI receiving coil, and the MRI receiving coil is placed in the MRI scanner isocenter. In another embodiment, the apparatus further comprises an MRI-compatible heater configured to be coupled to the cell chamber.

The apparatus provides for increased imaging resolution and signal-to-noise ratio. The apparatus minimizes the distance between the imaged cells and the receiving coil by adapting a cell chamber to fit inside the MRI receiving coil and/or adapting the receiving coil to the geometry of the cell chamber. The apparatus and methods may employ the electrophysiological activity of cells to trigger the MRI scanner and synchronize MR image acquisition to specific phases of cell activity cycle. Cell electrophysiological activity is recorded using MRI-compatible electrodes and may be analyzed in real time by the first processing unit to detect characteristic waveforms of electrophysiological activity and major (predominant) peaks, such as the main excitation peak (which is similar to the electrocardiographic R-peak on the surface electrocardiogram). In one embodiment, the times of such predominant peaks of electrical excitation are then used to trigger the MRI scanner and synchronize MRI with specific phases of cell electrophysiological activity (cycle) and thus increase the signal-to-noise ratio. In another embodiment, the first processing unit transmits the times of pacing stimuli to the MRI scanner to synchronize the MRI with the times of pacing stimuli.

To increase the signal-to-noise ratio, images may be obtained repeatedly during the same phase of, for example, the cardiac, cycles and averaged. A sequence of thus obtained and processed MR images that correspond to various phases of cells' electrophysiological activity cycle may be displayed on a computer screen to reproduce the speed and pattern of movement of cells, cell groups or subpopulations within cell populations (e.g., contractions).

In one embodiment, the methods and systems are employed for simultaneous mechanical and electrophysiologic imaging of MTCs. The methods may employ the magnetization and its relaxation-based measurements to determine the spatio-temporal distribution of cardiac electromagnetic field and cardiac electrical potential activities, and mechanical activity to record display and/or image. In one embodiment, the system uses external magnets, gradient magnetic fields and radio-frequency waves, such as those commonly used for MRI, to generate the magnetic resonance.

In one embodiment, a process for simultaneous tracking of both electrical excitation and mechanical contractions in mammalian MTCs on a cell-cluster scale is provided. The process employs MRI combined with MR-compatible electrophysiological imaging to synchronize (trigger) MRI pulse sequences to coincide with specific phases of electrophysiological activity (cycle). For example, rat (Sprague-Dawley) neonatal cardiomyocytes were isolated using the Worthington Neonatal Cardiomyocyte Isolation System (Worthington Biochemical Corp., Lakewood, N.J.) according to the manufacturer's instruction. Briefly, hearts were collected from one-day-old pups, minced, and digested with trypsin and collagenase sequentially. Cells were preplated to remove fibroblasts. The cardiomyocyte-enriched cells were placed on the testing plate embedded with MRI-compatible, flexible electrodes (PinMed, Inc., Pittsburgh, Pa.) in culture medium DMEM/F-12 with L-glutamine and HEPES containing 5% horse serum, 1×Gibco® Insulin-Transferrin-Selenium (ITS-G), and 1×penicillin-streptomycin (all from Life Technologies, Grand Island, N.Y.). The cardiomyocytes were cultured for 3-5 days in the same medium and used for imaging. For the electromechanical imaging, the testing plate was placed inside an MRI receiving coil and moved into the scanner isocenter.

MR imaging of mechanical activity in MTC may be performed, for example, on a Siemens Trio 3T scanner with the testing plate placed inside the head coil, e.g., a 8-channel head coil. Other devices may be employed for imaging mechanical activity. A two-dimensional, gradient-echo CINE sequence may he applied using the following parameters: flip angle: 65°; TR: 7.56 ms, TE: 1.89 ms, slice thickness: 5 mm. imaging frequency: 123.2561 Hz, number of phase encoding steps: 160, bandwidth: 965. However, each of these parameters may be varied. The CINE images may be sampled at 1-second intervals divided into 78 segments, which yield effective resolution of approximately 12.8 ms. Each image may be digitized using a 192×192 matrix and upsampled to a 384×384 matrix after application of an adaptive low-pass filter (for instance, Wiener filter with 3×3-pixel window).

To expose the patterns of cardiac contractions and estimate the contraction-wave propagation velocity, the local maxima (LM) of the image intensity gradients may be computed using the derivative of a Gaussian filter (standard deviation: 2.34 mm) applied to the ROI and depicted as contour curves. The contraction waves' velocity in the ROI may be evaluated in a horizontal, left-to-right direction along the spread of contraction waves from the pacing electrodes. First, the location of the left-most LM (closest to the pacing electrodes) is determined in each row of the ROI matrix in each consecutive CINE image. Then the differences between LM in each row are computed for all consecutive CINE images, and the mean and standard deviation of positive derivatives (which correspond the left-to-right wave movement) are determined.

MR-compatible electrophysiological mapping may be conducted using an MRI-compatible electrodes and electrophysiological recording system (e.g., one from PELEX-MR and PELEX-MAX, PinMed, Inc.), for continuous data recording during electromechanical imaging experiments.

The MTCs having cardiomyocytes may exhibit spontaneous mechanical contractions at approximately 30-60 bpm, which is similar to that in previous reports of MTCs. The contractions may be synchronized in clusters of cells of approximately 1-4 mm, but the clusters are not necessarily synchronized with each other. Pacing (0.5-2V) at 60-120 bpm may produce synchronous beating of all cell clusters on the plate. The electrophysiological recordings obtained from paced MTCs may demonstrate sharp, high-amplitude activation (depolarization) waves and rounded, low-amplitude recovery (repolarization) waves. During pacing, the MR image sequences may show repetitive waves of contractions that emanate from the pacing electrodes.

The estimates of electrophysiological activity that are used with a small number of recording electrodes in the three-dimensional electromechanical map may be sharpened by increasing the number and density of the MR-compatible electrodes The spatial resolution of MR imaging may be increased by using a receiving MR coil that closely fits the testing plate. This allows tracking of electromechanical activity in smaller-size cell clusters, as well as reconstructing global activity pattern with higher precision.

Further provided is an apparatus for simultaneously detecting mechanical activity and electrical activity in cells in vitro. The apparatus includes a cell chamber configured to contain cells; a plurality of electrodes configured to be coupled to the cell chamber to record the electrical activity; and a recording system including a magnetic resonance imaging (MRI) scanner configured to record the mechanical activity and an electrophysiological recording device configured to be coupled to recording electrodes of the plurality of electrodes to record the electrical activity, wherein the cell chamber, the plurality of electrodes, and the electrophysiological recording device are MRI compatible.

In one embodiment, the recording system is configured to conduct electromechanical mapping allowing for evaluation of coupling between electrical excitation and mechanical contraction properties of the cells. In one embodiment, the cell chamber comprises a substrate configured to contain the cells and a medium. In one embodiment, the plurality of electrodes comprises electrodes placed on the media. In one embodiment, the plurality of electrodes are each attached to the substrate. In one embodiment, the plurality of electrodes are each embedded in the substrate. In one embodiment, the plurality of electrodes comprises at least two pacing electrodes suitable for delivering cardiac pacing pulses to the cells, and further comprising a pacemaker configured to deliver the cardiac pacing pulses to the cells through the at least two pacing electrodes.

The invention will be further described by the following non-limiting example.

EXAMPLE

Contractions of cardiac tissues are triggered by electrical excitation of cardiomyocytes. The patterns of electrical and mechanical activity and the coupling between them are essential for normal functioning of the heart; their disruption usually signifies a diseased state. Cultured multicellular preparations (here collectively referred to as multicellular tissue constructs, MTCs) serve as models for studying electrical and mechanical properties of cardiac tissues in controlled conditions that replicate salient features of their natural environment, providing insight into the normal physiology and pathogenesis of heart diseases. In particular, they provide models for studying the mechanisms of cardiac arrhythmias and heart failure and serve as a tool for investigating the effects of molecular, genetic, pharmacological, and nonpharmacological interventions (Zlochiver et al., 2008).

Both electrical excitation and mechanical contraction, as well as their coupling, are central to cardiac functioning. While on a global scale mechanical contraction in the heart seems to follow closely behind electrical excitation after a short time lag (electromechanical delay) of 20-40 ms, a more detailed examination shows that the delay is nonuniform across the myocardial tissues; it is affected by excessive mechanical stretch and heterogeneity of contraction and is exacerbated in heart failure (Costet et al., 2014; Furev et al., 2010). Thus, an optimal monitoring modality must provide sufficient detail for the simultaneous tracking of both electrical excitation and mechanical contraction.

However, MTC monitoring is currently limited to the tracking of electrophysiological activity (using microelectrodes, their arrays, or optical imaging) and mechanical activity (using various types of microscopy) or its downstream sequelae (using force or pressure transducers). Although these techniques have been instrumental for studying two-dimensional MTCs, they are not scalable for three-dimensional constructs or for noninvasive in vivo imaging.

MTCs and MRI-Compatible Chamber

Rat (Sprague-Dawley) neonatal cardiomyocytes were isolated using the Worthington Neonatal Cardiomyocyte Isolation System (Worthington Biochemical Corp., Lakewood, N.J.) according to the manufacturer's instructions. Briefly, hearts were collected from one-day-old pups, minced, and digested with trypsin and collagenase sequentially. Cells were preplated to remove fibroblasts. The cardiomyocyte-enriched cells were placed on the testing plate (FIG. 2) embedded with MRI-compatible electrodes (PinMed, Inc., Pittsburgh, Pa.) in culture medium DMEM/F-12 with L-glutamine and HEPES containing 5% horse serum, 1×Gibco® Insulin-Transferrin-Selenium (ITS-G), and 1×penicillin-streptomycin (all from Life Technologies, Grand Island, N.Y.). The cardiomyocytes were cultured for 3-5 days in the same medium and used for imaging. For the electromechanical imaging experiments, the testing plate was placed inside an MRI receiving coil and moved into the scanner isocenter.

MRI of Mechanical Activity in MTC

Figure 3:
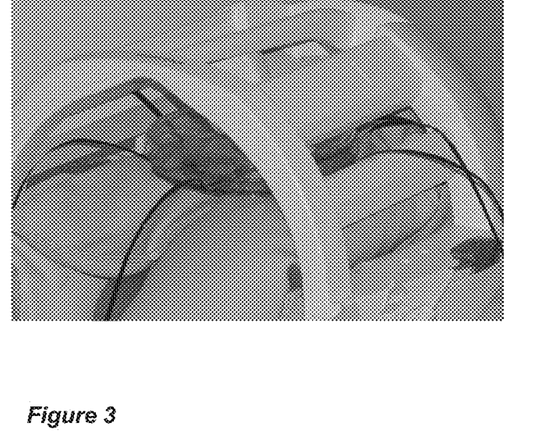
FIG. 3. Cell chamber with MRI-compatible recording and pacing electrodes placed inside a MRI receiving coil.

Imaging was performed on a Siemens Trio 3T scanner with the testing plate placed inside the 8-channel head coil (FIG. 3). The two-dimensional, gradient-echo CINE sequence was applied using the following parameters: flip angle: 65°; TR: 7.56 ms, TE: 1.89 ms, slice thickness: 5 mm, imaging frequency: 123.2561 Hz, number of phase encoding steps: 160, bandwidth: 965. The CINE images were sampled at 1-sec intervals divided into 78 segments, which yielded effective resolution of approximately 12.8 ms. Each image was digitized using a 192×192 matrix and upsampled to a 384×384 matrix after application of an adaptive low-pass filter (Wiener filter with 3×3-pixel window).

Figure 4:
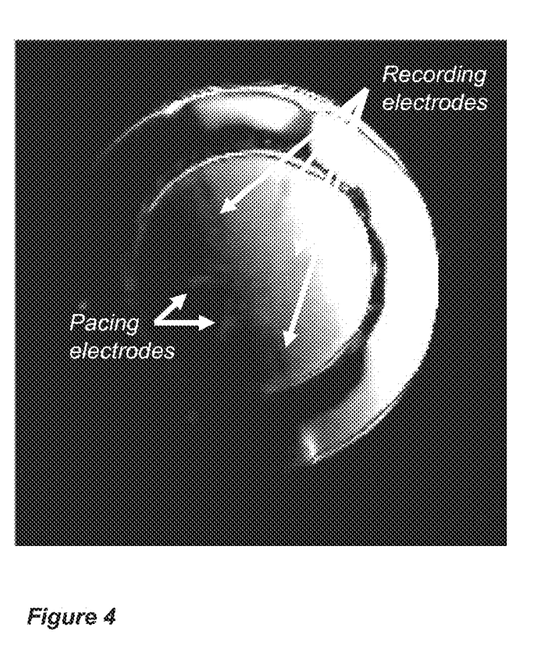
FIG. 4. MR image of the cell chamber and electrodes.
Figure 5:
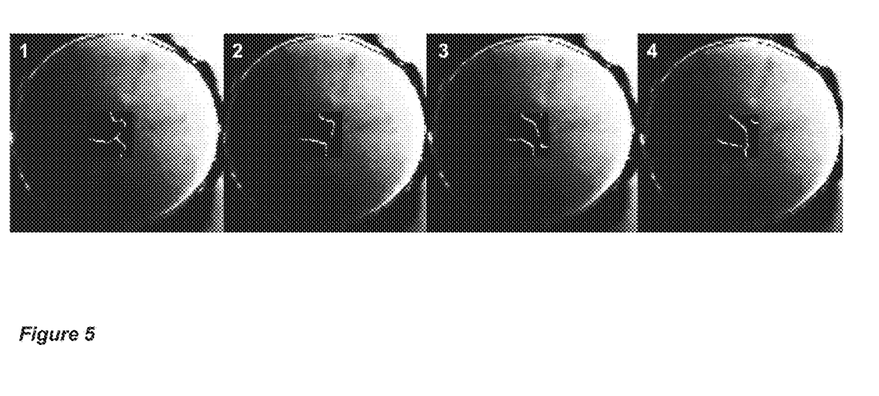
FIG. 5. The sequence of MR images obtained at 12.8-ms intervals with contours representing the local maxima of the image intensity gradients (computed using the derivative of a Gaussian filter) in the region of interest (ROI).

FIG. 4 shows an example of an MRI MTC preparation image. To expose the patterns of cardiac contractions and estimate the contraction-wave propagation velocity, the local maxima (LM) of the image intensity gradients were computed using the derivative of a Gaussian filter (standard deviation: 2.34 mm) applied to the region of interest (ROI) and depicted as contour curves (FIG. 5).

Two adjacent electrodes were used for electrical pacing (1 Hz, 0.5-2 V) as shown in FIG. 2; the rest of the electrodes were used for data recording. During pacing, the MR image sequences showed repetitive waves of contractions (movements) that emanated from the pacing electrodes (FIG. 5).

The contraction waves' velocity in the ROI was evaluated in a horizontal, left-to-right direction along the spread of contraction waves from the pacing electrodes. First, the location of the left-most LM (closest to the pacing electrodes) was determined in each row of the ROI matrix in each consecutive CINE image. Then the differences between LM in each row were computed for all consecutive CINE images, and the mean and standard deviation of positive derivatives (which correspond the left-to-right wave movement) were determined. The contraction velocity was estimated as:

$$CV = \frac{PD}{MD_{LM} \times TI},$$

where PD is the pixel-to-pixel distance (0.47 mm), $MD_{LM}$ is the mean positive difference between LM in consecutive CINE images for all rows in the ROI matrix, and TI is the time interval between consecutive CINE images (12.8 ms).

MRI-Compatible Electrophysiological Recording

Figure 6:
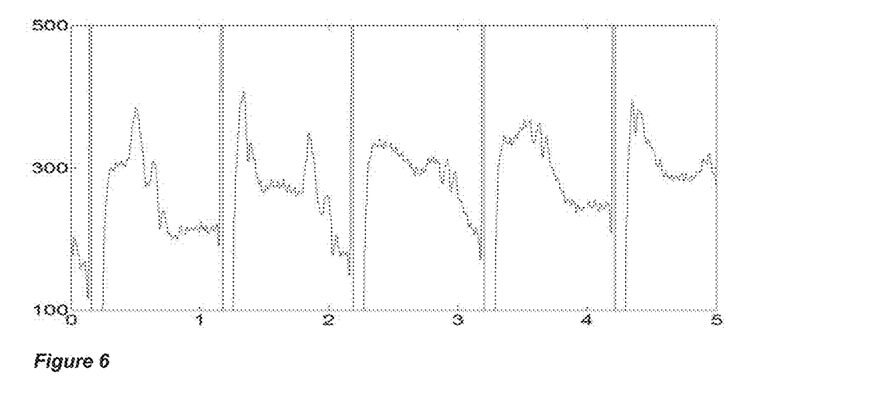
FIG. 6. Patterns of electrophysiological activity during pacing at 1 Hz. Note fractionated patterns with multiple, short-terms "bumps," which were associated with complex wave patterns of mechanical activity in the MR images.
Figure 7:
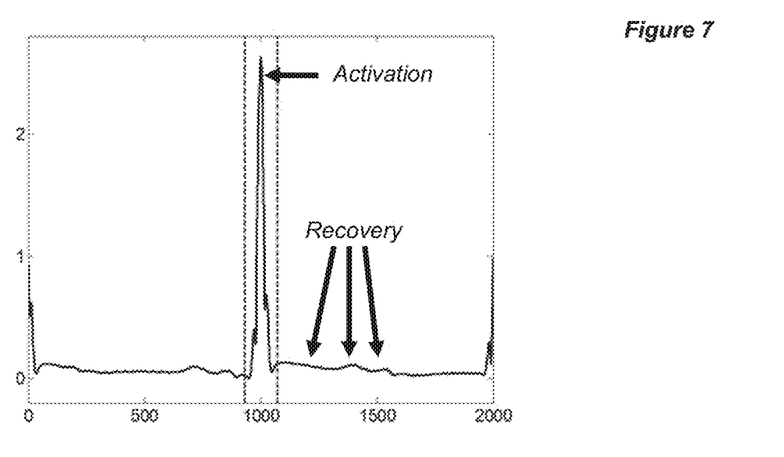
FIG. 7. An average electrophysiological activity complex on the root-mean-square (RMS) curve. The duration of the activation complex was measured between the dashed lines.

An MRI-compatible, wireless, 12-lead electrophysiological recording system (PELEX-MR, PinMed, Inc.) was used for continuous data recording during electromechanical imaging experiments. The data were recorded at 1 kHz/channel with 16-bit resolution (FIG. 6). The root-mean-square (RMS) curves were constructed from four individual channels:

$$RMS(t) = \sqrt{\frac{\sum_{i=1}^{4} v_i^2(t)}{4}}$$

where $v_i$ is the voltage in electrophysiological channel i. The conduction velocity (CV) was estimated as:

$$CV = \frac{D_e}{t_c},$$

where $D_e$ is distance between recording electrodes (30-33 mm) and $t_c$ is the activation (depolarization) time interval (FIG. 7).

This example shows that patterns of mechanical contraction development in MTCs can be tracked in sufficient detail using MRI despite the ultrathin profile (1-2 cell layers) and the small magnitude of the contractions. Combining such tracking with MR-compatible electrophysiological recording (imaging) creates new opportunities for evaluating the coupling between electrical excitation and mechanical contraction properties on a cell-cluster scale. The contraction wave displacements, direction and velocity, the key parameters required for the evaluation of strain and contractility in cell clusters, can be estimated using the dynamics of the LM of the image intensity gradients in serial MR images (FIG. 5) This combined imaging modality could be particularly useful for gaining insight into the mechanisms of heart failure because of its typical loss of spatial synchrony in cardiac muscle contractions and exaggerated and inhomogeneous electromechanical delays.

The spatial resolution of MRI also can be increased by constructing a receiving MR coil designed to fit the testing plate. This allows for tracking of electromechanical activity in smaller-size cell clusters, as well as reconstructing global activity patterns with higher precision.

REFERENCES

Costet et al., *Ultrasound Med. Biol.*, 40:177 (2014).
Mizutani and Suzuki, Y (2012). "X-ray microtomography in biology". *Micron*, 43:104 (1993).
Perkel, *Science*, 12 Jun. 2015 DOI: 10/1126/science/Opns.p150009.
Zlochiver et al., *Biophys J.*, 95:4469 (2008).

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. A method for dynamical imaging of cell movements, comprising:
   providing a cell chamber containing a population of cells positioned within a short distance from an MRI receiving coil;
   performing at least one operation selected from electrical pacing and recording of said cell population electrical activity using MRI-compatible electrodes in direct electrical contact with the said cell population;
   determining electrophysiological activity of said cell population from at least one signal selected from said electrical pacing and electromechanical activity of said cell population;
   triggering the MRI scanner to synchronize MRI with said phases of electrophysiological activity of said cell population and collecting sequential MR images during specific phases of cell electrophysiological activity; and
   displaying said sequential MR images on a screen at short time intervals to reproduce the speed and pattern of cell movements.

2. The method of claim 1 wherein said sequential MR images are obtained within a single cycle of electrophysiological activity.

3. The method of claim 1 wherein said sequential MR images are obtained within a single cycle of electrophysiological activity using a single MRI pulse sequence.

4. The method of claim 1 wherein said sequential MR images are obtained by passive data recording without using MRI pulse sequences.

5. The method of claim 1 wherein the population of cells is in a monolayer.

6. The method of claim 1 wherein the population of cells forms a bilayer on the substrate.

7. The method of claim 1 wherein the cells or media are in communication with the MRI-compatible electrodes.

8. The method of claim 1 wherein the cells are selected from cardiomyocytes, smooth muscle cells, neurons, skeletal muscle cells, stem cells, induced pluripotent stem cells (iPSCs), or from a human with a cardiac disorder.

9. The method of claim 1 wherein the cells are genetically modified.

10. The method of claim 1 wherein the cells are exposed to one or more compounds prior to simultaneous imaging and recording.

11. The method of claim 1 wherein the patterns of electrical excitation are recorded and the patterns of mechanical contractions are imaged.

12. The method of claim 1 wherein the one or more electrodes are embedded in or attached to the substrate.

13. The method of claim 1 wherein MR-based sodium, potassium or phosphorus imaging is employed.

14. An apparatus for dynamical imaging of cardiac cell movements, comprising:

a cell chamber for placing a population of cells within a short distance from an MRI receiving coil;

a plurality of electrodes configured to be placed in direct electrical contact with the cell population and performing at least one operation selected from electrical pacing and recording of the cell population electrophysiological activity;

a first processing unit for recording and analyzing said cell population electrical activity, determining time phases of cell electrical activity (activity cycle), and synchronizing MRI with said phases of cell activity cycle; and a second processing unit for processing and displaying MR images of cell positions during different phases of said activity cycle to reproduce cell movements.

15. The apparatus of claim 14 wherein the second processing unit is configured to calculate the delay between different phases of said cell electrophysiological activity determined by the first processing unit and cell movements determined from said MR images obtained during different phases of cell activity.

16. The apparatus of claim 14 wherein the cell chamber comprises a substrate configured to contain the cells and a medium.

17. The apparatus of claim 14 further comprising an MRI-compatible configured to be coupled to the cell chamber.

18. The apparatus of claim 14 further comprising MRI-compatible conduits for introducing and removing media from the substrate in the cell culture device.

19. The apparatus of claim 14 wherein at least one of the MRI receiving coil or cell chamber is adapted to provide the minimal distance between the MRI coil and the cells.

* * * * *

UNITED STATES PATENT AND TRADEMARK OFFICE
CERTIFICATE OF CORRECTION

PATENT NO. : 9,891,301 B2
APPLICATION NO. : 15/267868
DATED : February 13, 2018
INVENTOR(S) : London et al.

Page 1 of 1

It is certified that error appears in the above-identified patent and that said Letters Patent is hereby corrected as shown below:

On the Title Page

In Column 2, under "Other Publications", Line 2, delete "matix" and insert --matrix-- therefor On page 2, in Column 1, under "Other Publications", Line 1, delete ""Electromechanicalwave" and insert --"Electromechanical wave-- therefor On page 2, in Column 1, under "Other Publications", Line 2, delete "Biologicallyand" and insert --Biologically and-- therefor In the Specification

In Column 6, Line 62, delete "he" and insert --be-- therefor

In Column 10, Line 16, after "5)", insert --.--

In the Claims

In Column 12, Line 25, in Claim 17, before "configured", insert --heater--

Signed and Sealed this
Twenty-third Day of July, 2019

Andrei Iancu
*Director of the United States Patent and Trademark Office*